US009750519B2

(12) United States Patent
Garrison et al.

(10) Patent No.: US 9,750,519 B2
(45) Date of Patent: Sep. 5, 2017

(54) COUPLING MECHANISMS FOR SURGICAL INSTRUMENTS

(71) Applicant: COVIDIEN LP, Mansfield, MA (US)

(72) Inventors: David M. Garrison, Longmont, CO (US); Edward M. Chojin, Boulder, CO (US); Duane E. Kerr, Loveland, CO (US); Peter M. Mueller, Frederick, CO (US); Allan J. Evans, Golden, CO (US); James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/807,310

(22) Filed: Jul. 23, 2015

(65) Prior Publication Data
US 2015/0327879 A1    Nov. 19, 2015

Related U.S. Application Data

(63) Continuation of application No. 13/306,523, filed on Nov. 29, 2011, now Pat. No. 9,113,899.

(51) Int. Cl.
*A61B 17/285* (2006.01)
*A61B 18/14* (2006.01)
(Continued)

(52) U.S. Cl.
CPC ........ *A61B 17/285* (2013.01); *A61B 18/1445* (2013.01); *A61B 18/1482* (2013.01);
(Continued)

(58) Field of Classification Search
CPC ........ A61B 18/1445; A61B 2017/0046; A61B 2017/00473; A61B 2017/00477; A61B 2017/2931; A61B 2017/320016
See application file for complete search history.

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462        9/2009
DE    2415263 A1    10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Julie A Szpira

(57) ABSTRACT

A surgical instrument includes a shaft defining a longitudinal axis therethrough and having an end effector assembly disposed at a distal end thereof. The shaft includes first and second shaft components that are releasably engageable with one another. A drive sleeve is disposed within the shaft and is longitudinally translatable relative to the shaft to transition the end effector assembly between a first state and a second state. The drive sleeve includes first and second drive sleeve components that are releasably engageable with one another. A coupling mechanism includes one or more shaft cantilever springs configured to releasably engage the first and second shaft components to one another and one or more drive sleeve cantilever springs configured to releasably engage the first and second drive sleeve components to one another.

6 Claims, 9 Drawing Sheets

(51) Int. Cl.
*A61B 17/29* (2006.01)
*A61B 17/00* (2006.01)
*A61B 17/32* (2006.01)

(52) U.S. Cl.
CPC .......... A61B 2017/0046 (2013.01); A61B 2017/00473 (2013.01); A61B 2017/00477 (2013.01); A61B 2017/292 (2013.01); A61B 2017/2925 (2013.01); A61B 2017/2931 (2013.01); A61B 2017/320052 (2013.01); Y10T 74/18896 (2015.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| 5,391,166 A * | 2/1995 | Eggers | 606/48 |
| D358,887 S | 5/1995 | Feinberg | |
| 5,478,351 A | 12/1995 | Meade et al. | |
| 5,603,723 A | 2/1997 | Aranyi et al. | |
| D384,413 S | 9/1997 | Zlock et al. | |
| H1745 H | 8/1998 | Paraschac | |
| 5,792,165 A * | 8/1998 | Klieman et al. | 606/170 |
| D402,028 S | 12/1998 | Grimm et al. | |
| D408,018 S | 4/1999 | McNaughton | |
| 5,893,875 A * | 4/1999 | O'Connor et al. | 606/205 |
| D416,089 S | 11/1999 | Barton et al. | |
| D424,694 S | 5/2000 | Tetzlaff et al. | |
| D425,201 S | 5/2000 | Tetzlaff et al. | |
| 6,074,386 A | 6/2000 | Goble et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 8,021,321 B2 * | 9/2011 | Zawacki | A61M 1/3653 604/29 |
| D649,249 S | 11/2011 | Guerra | |
| D649,643 S | 11/2011 | Allen, IV et al. | |
| 8,343,105 B2 * | 1/2013 | Windheuser | A61M 25/00 604/164.05 |
| 8,377,044 B2 * | 2/2013 | Coe et al. | 606/1 |
| 8,480,689 B2 * | 7/2013 | Spivey | A61B 17/06066 606/144 |
| 9,108,026 B2 * | 8/2015 | Deckard | A61B 17/22012 |
| 9,113,899 B2 | 8/2015 | Garrison et al. | |
| 2007/0016237 A1 | 1/2007 | Smith | |
| 2008/0243106 A1 * | 10/2008 | Coe et al. | 606/1 |
| 2009/0054894 A1 | 2/2009 | Yachi | |
| 2010/0049168 A1 * | 2/2010 | Parker et al. | 604/527 |
| 2011/0071522 A1 | 3/2011 | Dumbauld et al. | |
| 2013/0030416 A1 * | 1/2013 | Fernandes | A61M 25/0043 604/544 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 20 2007 009317 U1 | 8/2007 |
| DE | 202007009165 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 1738699 A1 | 1/2007 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2001-3400 | 11/2001 |
| JP | 2002-528166 A | 9/2002 |

(56) References Cited

FOREIGN PATENT DOCUMENTS

| | | |
|---|---|---|
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005/110264 A2 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.

(56) References Cited

OTHER PUBLICATIONS

Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report No. 12193997.9 dated Apr. 2, 2015, 6 pages.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.

* cited by examiner

COUPLING MECHANISMS FOR SURGICAL INSTRUMENTS

CROSS-REFERENCE TO RELATED APPLICATION

This application is a continuation of U.S. patent application Ser. No. 13/306,523 entitled "COUPLING MECHANISMS FOR SURGICAL INSTRUMENTS", filed Nov. 29, 2011, the contents of which are hereby incorporated by reference.

BACKGROUND

Technical Field

The present disclosure relates to surgical instruments and, more particularly, to coupling mechanisms for surgical instruments having separable and/or replaceable components.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts, that any disposable components of these instruments be efficiently removable and replaceable with new components, and that the reusable components be efficiently and satisfactorily sterilizable for reuse.

SUMMARY

As used herein, the term "distal" refers to the portion that is being described which is further from a user, while the term "proximal" refers to the portion that is being described which is closer to a user.

Any of the aspects disclosed herein, to the extent they are consistent, may be used in conjunction with any of the other aspects disclosed herein.

In accordance with one aspect of the present disclosure, a surgical instrument is provided. The surgical instrument includes a shaft defining a longitudinal axis therethrough and having an end effector assembly disposed at a distal end thereof. The shaft includes first and second shaft components that are releasably engageable with one another. A drive sleeve is disposed within the shaft and is longitudinally translatable relative to the shaft to transition the end effector assembly between a first state and a second state. The drive sleeve also includes first and second drive sleeve components that are releasably engageable with one another. A coupling mechanism includes one or more shaft cantilever springs and one or more drive sleeve cantilever springs that are coupled to the one or more shaft cantilever springs. The shaft cantilever springs are configured to engage the first shaft component at a first end thereof and the second shaft component at a second end thereof to releasably engage the first and second shaft components to one another. Similarly, the drive sleeve cantilever springs are configured to engage the first drive sleeve component at a first end thereof and the second drive sleeve component at a second end thereof to releasably engage the first and second drive sleeve components to one another.

In one aspect, the shaft cantilever springs include a first tab disposed at the first end thereof and extending therefrom and a second tab disposed at the second end thereof and extending therefrom. The first tab and second tabs are configured to bias into engagement within apertures defined within the first and second shaft components, respectively, to engage the first and second shaft components to one another. Further, the drive sleeve cantilever springs may also include a first tab disposed at the first end thereof and extending therefrom and a second tab disposed at the second end thereof and extending therefrom. The first tab and second tabs are configured to bias into engagement within apertures defined within the first and second drive components, respectively, to engage the first and second drive sleeve components to one another.

In another aspect, the shaft cantilever spring and the drive sleeve cantilever spring are coupled to one another via a break-away feature. The break-away feature is configured to break, decoupling the shaft cantilever spring and the drive sleeve cantilever spring from one another to permit the drive sleeve to translate relative to the shaft.

In still another aspect, a knife assembly is disposed within the drive sleeve. The knife assembly includes a knife bar having a knife disposed at a distal end of the knife bar. The knife bar is longitudinally translatable through the shaft and relative to the end effector assembly to translate the knife between a retracted position and an extended position for cutting tissue.

Another aspect of a surgical instrument provided in accordance with the present disclosure includes a shaft defining a longitudinal axis therethrough and having an end effector assembly disposed at a distal end thereof. The shaft includes first and second shaft components that are releasably engageable with one another. The first shaft component includes a tab disposed on an outer surface thereof and extending outwardly therefrom, while the second shaft component includes a track defined within an outer peripheral surface thereof. The track includes a longitudinal portion, a transverse portion, and a tab retaining portion. The first shaft component is configured for insertion at least partially into the second shaft component such that the tab is translated along the longitudinal portion of the track into position adjacent the transverse portion of the track. The first shaft component is then rotatable about the longitudinal axis and relative to the second shaft component to translate the tab along the transverse portion of the track and into the tab retaining portion for releasably engaging the first and second shaft components to one another.

In one aspect, a biasing member configured to bias the first and second shaft components apart from one another is provided. The biasing member biases the tab into engagement within the tab retaining portion of the track to maintain the first and second shaft components in engagement with one another.

In another aspect, the first and second shaft components are configured to permit translation of a drive sleeve therethrough for transitioning the end effector assembly between a first state and a second state.

In yet another aspect, the surgical instrument further includes a knife assembly disposed within the drive sleeve. The knife assembly includes a knife bar having a knife disposed at a distal end of the knife bar and is longitudinally translatable through the shaft and relative to the end effector assembly to translate the knife between a retracted position and an extended position for cutting tissue.

Still another aspect of a surgical instrument provided in accordance with the present disclosure includes a shaft defining a longitudinal axis therethrough and having an end effector assembly disposed at a distal end thereof. The shaft includes first and second shaft components that are releasably engageable with one another. The first shaft component includes an insertion portion, while the second shaft component includes a receiving portion configured to receive the insertion portion of the first shaft component therein to frictionally engage the first and second shaft components to one another. The receiving portion is configured to constrict about the insertion portion upon translation of the insertion portion apart from the receiving portion to inhibit withdrawal of the insertion portion, thereby maintaining the engagement between the first and second shaft components.

In one aspect, receiving portion defines a braided configuration configured to elongate and reduce a diameter of a lumen extending therethrough upon extension of the receiving portion.

In another aspect, the insertion portion defines a textured outer peripheral surface configured to facilitate frictional engagement between the insertion portion and the receiving portion.

In still another aspect, a release ring is provided. The release ring is disposed about the first shaft component and is slidable about the first shaft component into position adjacent the receiving portion of the second shaft component to inhibit constriction of the receiving portion about the insertion portion, thereby permitting withdrawal of the insertion portion from the receiving portion to disengage the first and second shaft components from one another. The surgical instrument may further be configured similar to any of the previous aspects mentioned hereinabove.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
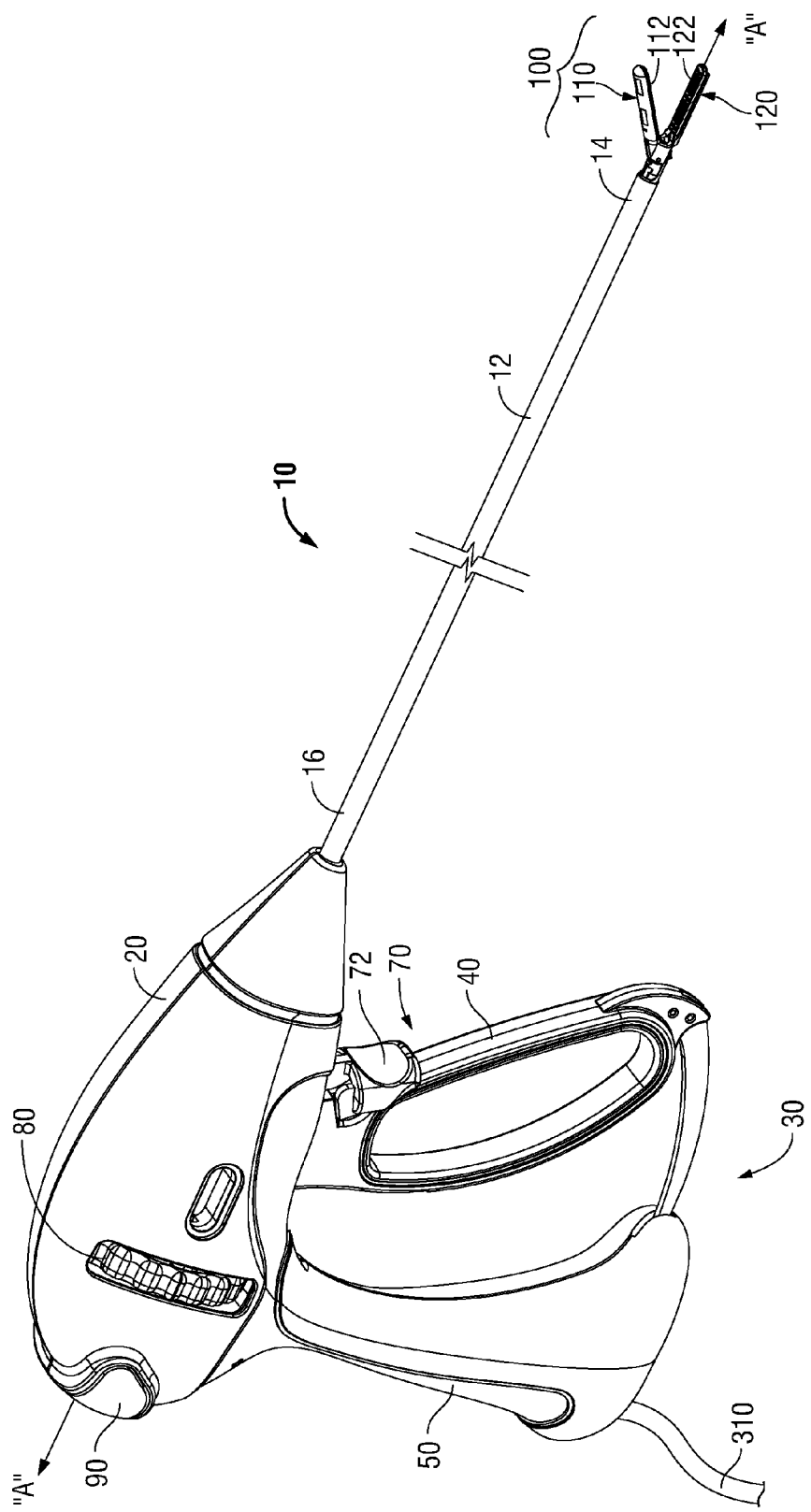
FIG. 1 is a side, perspective view of one embodiment of a surgical instrument provided in accordance with the present disclosure wherein the shaft of the instrument is in an assembled condition.

Referring now to FIG. 1, a forceps 10 for use in connection with endoscopic surgical procedures is shown, although forceps 10 may also be configured for use in connection with traditional open surgical procedures. Forceps 10 defines a longitudinal axis "A-A" and includes a housing 20, a handle assembly 30, a trigger assembly 70, a rotating assembly 80, and an end effector assembly 100. End effector assembly 100 includes first and second jaw members 110, 120, respectively, configured to pivot relative to one another between a spaced-apart position (FIG. 1) and an approximated position (FIG. 8B) for grasping tissue therebetween. Forceps 10 further includes a shaft 12 having a distal end 14 configured to mechanically engage end effector assembly 100 and a proximal end 16 that mechanically engages housing 20.

Forceps 10 also includes an electrosurgical cable 310 that connects forceps 10 to a generator (not shown) or other suitable power source, although forceps 10 may alternatively be configured as a battery powered instrument. Cable 310 includes a wire (or wires) (not explicitly shown) extending therethrough, into housing 20 and through shaft 12 to ultimately connect the source of electrosurgical energy (not explicitly shown) to jaw member 110 and/or jaw member 120 of end effector assembly 100. However, any other suitable electrical connection(s) for supplying energy to jaw member 110 and/or jaw member 120 may also be provided.

With continued reference to FIG. 1, handle assembly 30 includes a fixed handle 50 and a moveable handle 40. Fixed handle 50 is integrally associated with housing 20 and handle 40 is moveable relative to fixed handle 50. Rotating assembly 80 is rotatable in either direction about a longitudinal axis "A-A" to rotate end effector 100 about longitudinal axis "A-A." The housing 20 houses the internal working components of the forceps 10.

End effector assembly 100 is attached at a distal end 14 of shaft 12 and includes a pair of opposing jaw members 110 and 120. End effector assembly 100 is designed as a unilateral assembly, i.e., where jaw member 120 is fixed relative to shaft 12 and jaw member 110 is moveable relative to both shaft 12 and fixed jaw member 120. However, end effector assembly 100 may alternatively be configured as a bilateral assembly, i.e., where both jaw member 110 and jaw member 120 are moveable relative to one another and with respect to shaft 12.

As shown in FIG. 1, each jaw member 110, 120 includes an electrically conductive tissue sealing plate 112, 122 disposed thereon. Tissue sealing plates 112, 122 are positioned on jaw members 110, 120, respectively, to define opposed tissue sealing surfaces for grasping and sealing tissue between jaw members 110, 120. In some embodiments, a knife assembly 180 (see FIGS. 2A-2C) is disposed within shaft 12 and a knife channel 115, 125 (FIGS. 2A-2C) is defined within one or both of tissue sealing plates 112, 122, of jaw members 110, 120, respectively, to permit reciprocation of a knife 184 (see FIGS. 2A-2C) therethrough for cutting tissue grasped between jaw members 110, 120. In such an embodiment, trigger 72 of trigger assembly 70 is operable to advance the knife 184 (FIGS. 2A-2C) between a retracted position (see FIGS. 2A-2B), wherein knife 184 (FIGS. 2A-2C) is disposed within shaft 12, and an extended position (see FIG. 2C), wherein knife 184 (FIGS. 2A-2C) extends between jaw members 110, 120 to cut tissue grasped therebetween.

Continuing with reference to FIG. 1, moveable handle 40 of handle assembly 30 is ultimately connected to a drive assembly including a drive sleeve 60 (FIG. 4) that, together, mechanically cooperate to impart movement of jaw members 110 and 120 between a spaced-apart position and an approximated position to grasp tissue between sealing plates 112 and 122 of jaw members 110, 120, respectively. As shown in FIG. 1, moveable handle 40 is initially spaced-apart from fixed handle 50 and, correspondingly, jaw members 110, 120 are disposed in the spaced-apart position. Moveable handle 40 is depressible from this initial position to a depressed position corresponding to the approximated position of jaw members 110, 120 (see FIGS. 2B-2C). With tissue grasped between tissue sealing plates 112, 122 of jaw members 110, 120, respectively, electrosurgical energy may be conducted between tissue sealing plates 112, 122, e.g., upon actuation of activation switch 90, to seal tissue disposed between jaw members 110, 120.

Figure 2A:
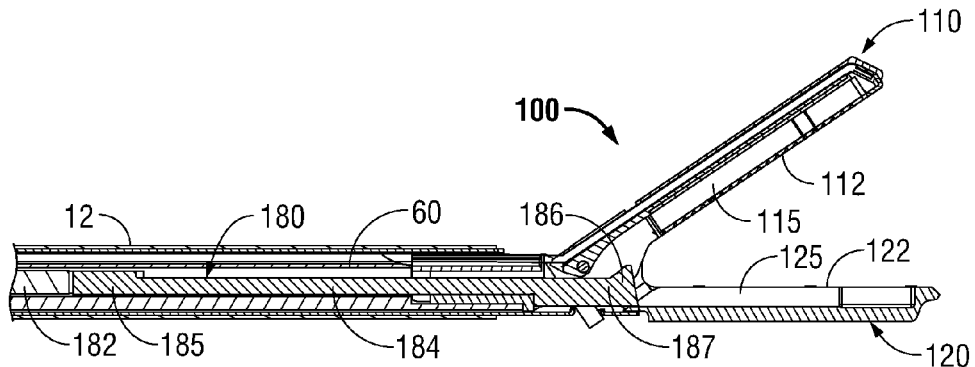
FIG. 2A is a longitudinal, cross-sectional view of the surgical instrument of FIG. 1 wherein an end effector assembly is disposed in a spaced-apart position.
Figure 2B:
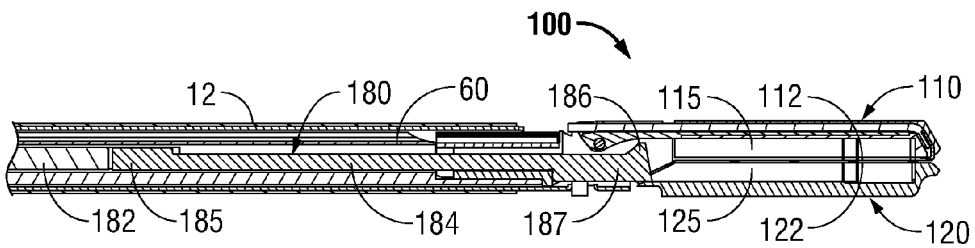
FIG. 2B is a longitudinal, cross-sectional view of the surgical instrument of FIG. 1 wherein the end effector assembly is disposed in an approximated position and wherein a knife blade is disposed in a retracted position.
Figure 2C:
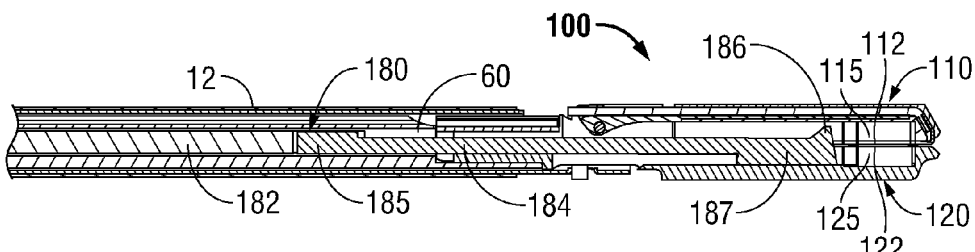
FIG. 2C is a longitudinal, cross-sectional view of the surgical instrument of FIG. 1 wherein the end effector assembly is disposed in an approximated position and wherein the knife blade is disposed in an extended position.

With reference now to FIGS. 2A-2C, in conjunction with FIG. 1, drive sleeve 60 is disposed within shaft 12 and is coupled to jaw member 110 at the distal end thereof such that, as drive sleeve 60 is translated proximally through shaft 12 and relative to jaw member 120, e.g., via depressing movable handle 40, jaw member 110 is pulled to pivot from the spaced-apart position (FIG. 2A) to the approximated position (FIGS. 2B, 2C). On the other hand, when drive sleeve 60 is translated distally, e.g., via releasing or returning movable handle 40 to its initial position, jaw member 110 is urged to pivot from the approximated position (FIGS. 2B, 2C) back to the spaced-apart position (FIG. 2A). However, this configuration may be reversed, e.g., where proximal translation of drive sleeve 60 moves jaw members 110, 120 to the spaced-apart position and wherein distal translation of drive sleeve 60 moves jaw members 110, 120 to the approximated position.

Continuing with reference to FIGS. 2A-2C, shaft 12 further includes a knife assembly 180 disposed therein. Knife assembly 180 is disposed within drive sleeve 60 and includes a knife bar 182 having knife 184 coupled thereto at the proximal end of 185 of knife 184. Knife 184 defines a cutting blade 186 at distal end 187 thereof. Knife 184 is translatable between a retracted position (FIGS. 2A-2B), wherein knife 184 is disposed within shaft 12, and an extended position (FIG. 2C), wherein knife 184 extends through knife channels 115, 125 defined within jaw members 110, 120, respectively, to cut tissue grasped between jaw members 110, 120. More specifically, upon actuation of trigger 72 (FIG. 1) of trigger assembly 70 (FIG. 1), knife bar 182 is advanced distally through shaft 12 and drive sleeve 60 to urge knife 184 from the retracted position to the extended position. Further, knife assembly 180 may be biased, e.g., via a spring (not explicitly shown), toward the retracted position such that, upon release of trigger 72, knife 184 is automatically returned to the retracted position.

Figure 3:
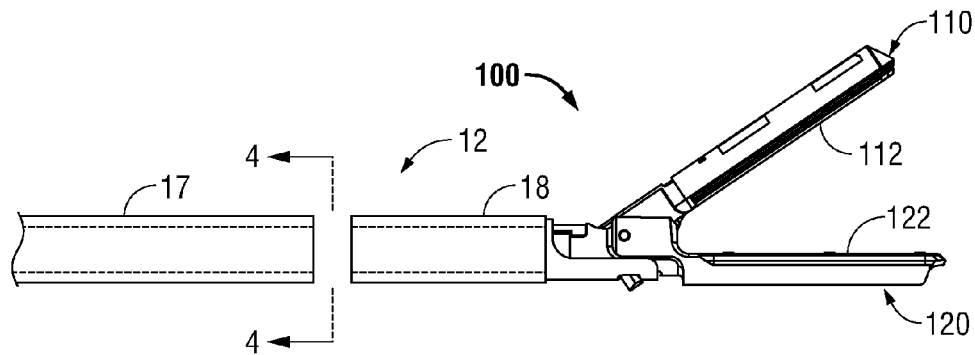
FIG. 3 is an enlarged, side view of a distal end of the surgical instrument of FIG. 1, wherein the shaft of the instrument is in a decoupled condition.
Figure 4:
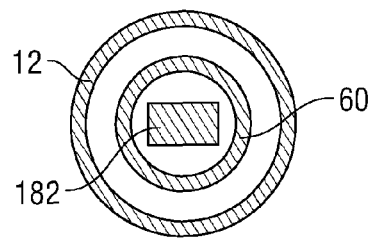
FIG. 4 is a transverse, cross-sectional view of the surgical instrument of FIG. 3 taken across section line 4-4.

Turning now to FIGS. 3-4, in conjunction with FIGS. 1-2C, shaft 12 of forceps 10 is separable, or decouplable into first and second shaft sections 17 and 18, respectively. More specifically, second section 18 of shaft 12, including end effector assembly 100, is removable from the remainder of forceps 10, thus allowing second section 18 of shaft 12 and end effector assembly 100 to be replaced with new components after each use (or each procedure), or to be cleaned, sterilized, or otherwise prepared for reuse independently of the remaining components of forceps 10. Such a configuration also permits the use of various different end effector assemblies with forceps 10 by simply selecting the desired end effector assembly and coupling that end effector assembly and the second shaft section 18 thereof to first section 17 of shaft 12.

Put more generally, the replaceable distal portion, e.g., second shaft section 18 and end effector assembly 100, of forceps 10 helps reduce the equipment costs associated with performing a particular surgical procedure by obviating the need to provide an entire new surgical instrument, facilities sterilization and cleaning of the components of the instrument by providing greater access to the components of the instrument and allowing different components of the instrument to be cleaned and/or sterilized via different procedures, and increases the versatility of the instrument by allowing different shaft components and/or end effectors to be coupled thereto.

However, while it is advantageous to provide a surgical instrument, e.g., forceps 10, that includes a shaft 12 that is separable into first and shaft sections 17 and 18, respectively, significant considerations apply when configuring a shaft coupling mechanism for releasably coupling first and second shaft sections 17, 18, respectively, to one another. In particular, it is important to consider the various components and connections extending through shaft 12. More specifically, as best shown in FIG. 4, shaft 12 defines an outer tube, or lumen that houses drive sleeve 60. Drive sleeve 60, as mentioned above, is selectively translatable through and relative to shaft 12 to pivot jaw member 110 relative to jaw member 120 between the spaced-apart and approximated positions. Drive sleeve 60 also includes knife bar 182 disposed therein that, as described above, is selectively translatable relative to drive sleeve 60 and shaft 12 to advance knife 184 from the retracted position to the extended position to cut tissue grasped between jaw members 110, 120. Further, electrical connections, e.g., wires (not explicitly shown), extend through shaft 12 to connect the source of electrosurgical energy (not explicitly shown) to jaw member 110 and/or jaw member 120 of end effector assembly 100 for providing energizing end effector assembly.

Various embodiment of coupling mechanisms configured to releasably couple the first and second sections 17 and 18, respectively, of shaft 12 to one another in accordance with those considerations addressed above will be described in detail below with reference to FIGS. 5A-15. More particularly, the coupling mechanisms described hereinbelow may be configured for coupling the first and second sections 17, 18 of shaft 12, the components of drive sleeve 60, and/or the components of knife bar 182 to one another, as well as for re-establishing and electrical connections extending through shaft 12. Further, the various coupling mechanisms described hereinbelow may be used alone or in combination with one another to releasably couple one or more of the respective components of shaft 12, drive sleeve 60, and/or knife bar 182 to one another. Thus, while certain coupling mechanisms may be shown and described with reference to only a single connection, e.g., for coupling the first and second sections 17, 18 of shaft 12 to one another, such mechanisms (or other coupling mechanisms) may also be used for further coupling the other components, e.g., first and second sections of the drive sleeve 60 and/or knife bar 182, to one another. Likewise, the electrical connections described hereinbelow in connection with some embodiments of coupling mechanisms for electrically coupling the first and second sections 17, 18, respectively, of shaft 12 to one another such that electrosurgical energy may be supplied from housing 20 to end effector assembly 100 may also be used in conjunction with any of the other coupling mechanisms described herein.

Additionally, although the embodiments herein are described with reference to a forceps 10, the presently disclosed coupling mechanisms may be used in conjunction with any shafted surgical instrument (including single or multiple component shafts) having an end effector assembly disposed at one end and a handle, housing, grip, control, etc. disposed at the other end. Further, the attachment point of first and second sections 17, 18, respectively, of shaft 12 may be disposed at various positions along the length of shaft 12, e.g., closer towards distal end 14 such that second section 18 defines a greater length than first portion 17, closer toward proximal end 16 such that first section 17 defines a greater length than first portion 17, or anywhere between proximal end 16 and distal end 14 of shaft 12.

Figure 5A:
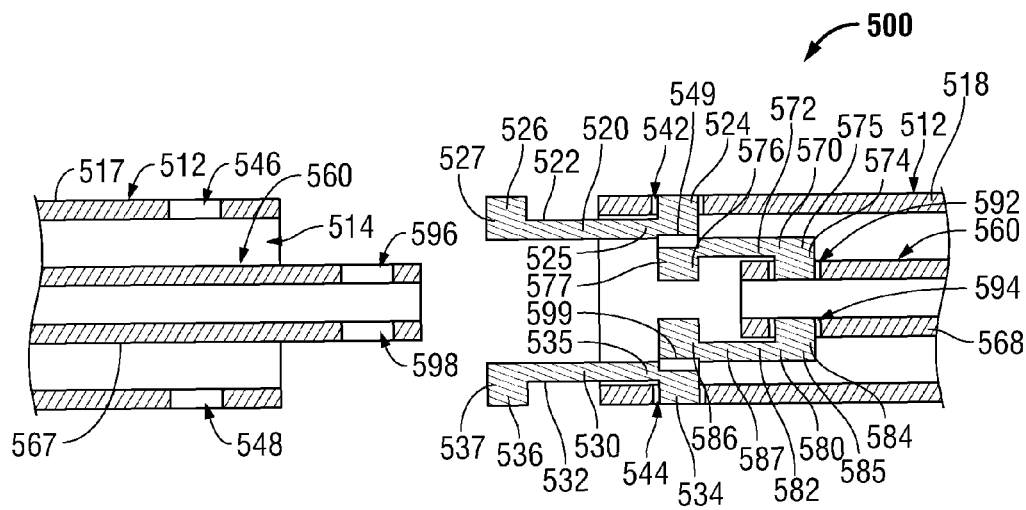
FIG. 5A is a side, cross-sectional view of one embodiment of a shaft coupling mechanism provided in accordance with the present disclosure wherein the shaft is in a decoupled condition.
Figure 5B:
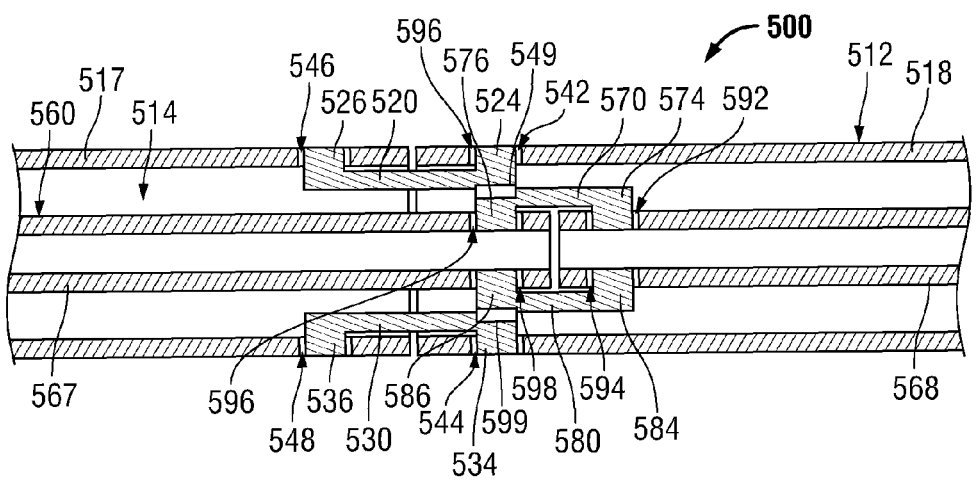
FIG. 5B is a side, cross-sectional view of the shaft coupling mechanism of FIG. 5A wherein the shaft is in an assembled condition.

Referring now to FIGS. 5A-5B, one embodiment of a tube coupling mechanism for coupling first and second components 517, 518, respectively, of shaft 512 to one another as well as for coupling first and second components 567, 568, respectively, of drive sleeve 560 to one another is shown generally identified by reference numeral 500. Tube coupling mechanism 500 includes two sets of cantilever springs 520, 530 and 570, 580. Each cantilever spring 520, 530 of the first set includes an arm 522, 532 that has a first tab 524, 534 disposed at a first end 525, 535, respectively, thereof and a second tab 526, 536 disposed at second end 527, 537, respectively, thereof. First tabs 524, 534 are engaged within apertures 542, 544, respectively, of second component 518 of shaft 512, while second tabs 526, 536 are configured for engagement within apertures 546, 548, respectively, defined within first component 517 of shaft 512. More specifically, as will be described below, cantilever springs 520, 530 are configured to resiliently bias second tabs 526, 536, respectively, into engagement with respective apertures 546, 548 of first component 517 upon insertion into shaft 512 to engage first and second components 517, 518, respectively, of shaft 512 to one another.

Each cantilever spring 570, 580 of the second set similarly includes an arm 572, 582 that has a first tab 574, 584 disposed at a first end 575, 585, respectively, thereof and a second tab 576, 586 disposed at second end 577, 587, respectively, thereof. First tabs 574, 584 are engaged within apertures 592, 594, respectively, of second component 568 of drive sleeve 560, while cantilever springs 570, 580 are configured to resiliently bias second tabs 576, 586, respectively, into engagement with respective apertures 566, 568 of first component 567 of drive sleeve 560 upon positioning about drive sleeve 560 to engage first and second components 567, 568, respectively, of drive sleeve 560 to one another. Further, cantilever springs 520, 570 may be coupled, engaged, or otherwise formed to one another adjacent first end 525 of cantilever spring 520 and second end 577 of cantilever spring 570 via a break-away feature, or coupling 549. Cantilever springs 530, 580 may likewise be coupled, engaged, or otherwise formed to one another adjacent first end 535 of cantilever spring 530 and second end 587 of cantilever spring 580 via a break-away feature, or coupling 599.

With continued reference to FIGS. 5A-5B, in order to couple first and second components 517, 518, respectively, of shaft 512 to one another and first and second components 567, 568, respectively, of drive sleeve 560 to one another, first and second component 517, 518 of shaft 512 are brought into approximation with one another. As can be appreciated, approximation of first and second component 517, 518 of shaft 512 likewise approximates first and second components 567, 568 of drive sleeve 560 due to the engagement of cantilever springs 520, 570 and 530, 580 via break-away couplings 549, 599, respectively. More specifically, as first and second component 517, 518 of shaft 512 are brought into approximation with one another, second tabs 526, 536 of cantilever springs 520, 530, respectively, are flexed inwardly, i.e., toward one another, to permit passage of cantilever springs 520, 530 into lumen 514 defined through shaft 512. On the other hand, second tabs 576, 586 of cantilever springs 570, 580, respectively, are flexed outwardly, i.e., apart from one another, to permit passage of cantilever springs 570, 580 about drive sleeve 560.

As first and second components 517, 518 of shaft 512 are further approximated relative to one another, second tabs 526, 536 of cantilever springs 520, 530, respectively, are eventually translated through lumen 514 of shaft 512 into position adjacent apertures 542, 544 of first component 517, whereby cantilever springs 520, 530 are resiliently biased back to their initial, un-flexed position, thus urging second tabs 526, 536 into engagement within apertures 542, 544, respectively, to engage first and second components 517, 518, respectively, of shaft 512 to one another. Similarly, second tabs 576, 586 of cantilever springs 570, 580, respectively, are eventually translated about the outer periphery of first component 567 of drive sleeve 560 into position adjacent apertures 592, 594 of first component 567, whereby cantilever springs 570, 580 are resiliently biased back to their initial, un-flexed position, thus urging second tabs 576, 586 into engagement within apertures 592, 594, respectively, to engage first and second components 567, 568, respectively, of drive sleeve 560 to one another.

With first and second components 517, 518 of shaft 512 engaged to one another and with first and second components 567, 568 of drive sleeve 560 engaged to one another, drive sleeve 560 may be translated relative to shaft 512 an initial time, e.g., via depressing movable handle 40 (FIG. 1), to break, tear, or otherwise destroy break-away couplings 549 and 599. As can be appreciated, with break-away couplings 549, 599 no longer securing cantilever springs 520, 270 to one another nor cantilever springs 530, 580 to one another, drive sleeve 560 is free to translate through lumen 514 and relative to shaft 512 for moving jaw members 110, 120 (FIG. 1) between the spaced-apart and approximated positions.

In order to decouple shaft components 517, 518 from one another, a tool (not shown) or other implement may be used to urge tabs 526, 536 inwardly such that tabs 526, 536 are no longer disposed within apertures 546, 548, respectively. With tabs 526, 536 removed from apertures 546, 548, shaft components 517, 518 may be translated apart from one another to decouple shaft component 517, 518 from one another. First and second components 567, 568 of drive sleeve 560 may similarly be decoupled from one another.

Figure 6A:
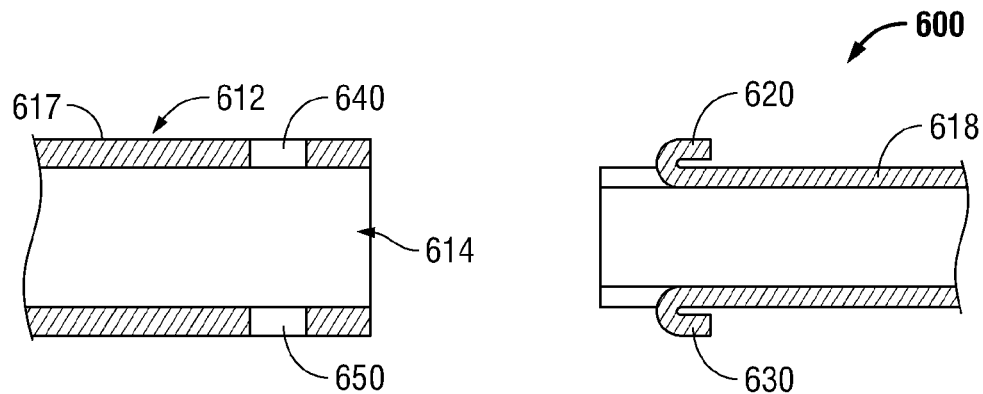
FIG. 6A is a side, cross-sectional view of another embodiment of a shaft coupling mechanism provided in accordance with the present disclosure wherein the shaft is in a decoupled condition.

Turning now to FIGS. 6A-6E, another embodiment of a tube coupling mechanism is shown generally identified via reference numeral 600. Tube coupling mechanism 600 is configured to releasably engage first and second components 617, 618 of shaft 612 to one another. More specifically, tube coupling mechanism 600 includes a pair of resilient locking tabs 620, 630 formed in the outer periphery of second component 618 and extending outwardly therefrom (although locking tabs 620, 630 may alternatively be formed on shaft component 617 to extend inwardly therefrom). As best shown in FIG. 6A, in an at-rest position, locking tabs 620, 630 are bent, or folded-back onto themselves and protrude from the outer periphery of second shaft component 618. Each locking tab 620, 630 defines a free end 622, 632, respectively, that permits resilient flexion of locking tabs 620, 630 relative to second shaft component 618. First shaft component 617, on the other hand, includes a pair of apertures 640, 650 configured to receive locking tabs 620, 630, respectively, therein. Further, first shaft component 617 may define a slightly larger diameter than second shaft component 618 such that second shaft component 618 may be inserted at least partially into lumen 614 of first shaft component 617 to couple first and second shaft components 617, 618, respectively, to one another, as will be described below.

Figure 6B:
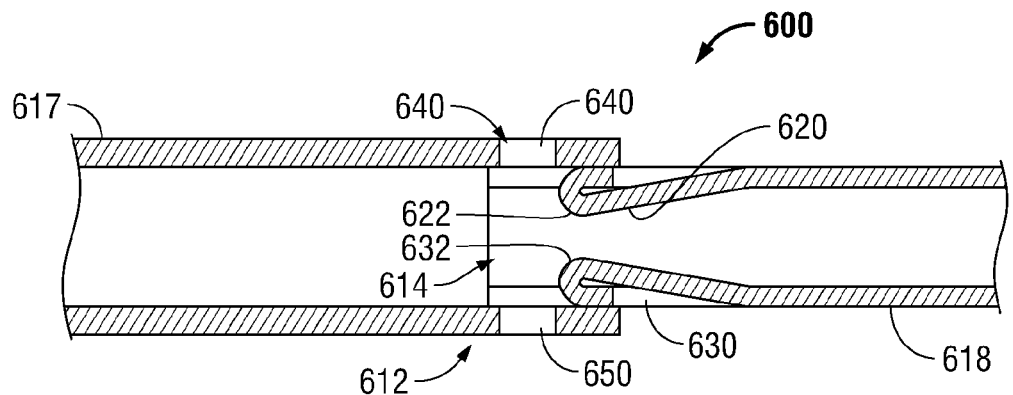
FIG. 6B is a side, cross-sectional view of the shaft coupling mechanism of FIG. 6A during assembly of the shaft.
Figure 6C:
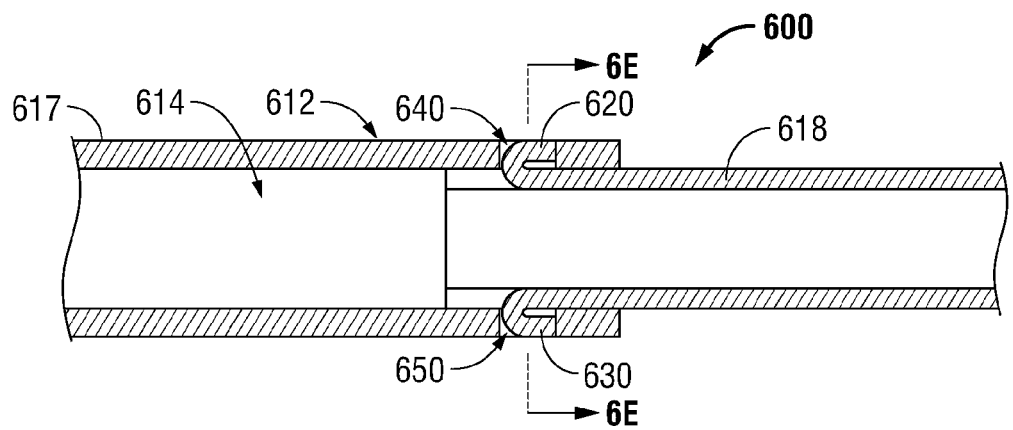
FIG. 6C is a side, cross-sectional view of the shaft coupling mechanism of FIG. 6A, wherein the shaft is in an assembled condition.
Figure 6D:
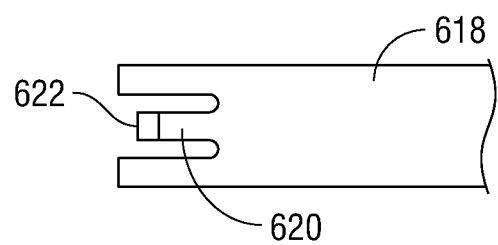
FIG. 6D is a top view of one of the shaft components of the shaft of FIG. 6A.
Figure 6E:
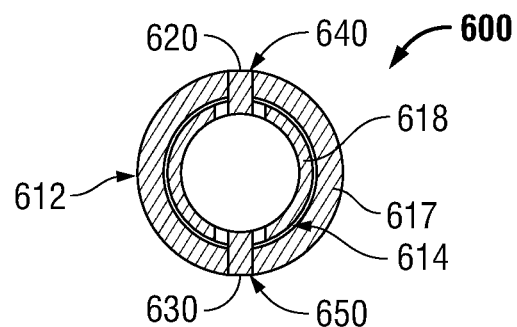
FIG. 6E is a transverse, cross-sectional view taken along section line 6E-6E of FIG. 6C.

With continued reference to FIGS. 6A-6E, in order to engage first and second shaft components 617, 618, respectively, to one another, second shaft component 618 is inserted into lumen 614 defined through first shaft component 617. As second shaft component 618 is urged into lumen 614 of first shaft component 617, resilient locking tabs 620, 630 are flexed, or compressed inwardly into second shaft component 618 in order to permit passage of second shaft component 618 into lumen 614 of first shaft component 617, as best shown in FIG. 6B.

As second shaft component 618 is translated further through lumen 614 of first shaft components 617 tabs 620, 630 are eventually translated into position adjacent apertures 640, 650 of first shaft component 617, whereby tabs 620, 630 are resiliently biased back to their initial, un-compressed position (extending from second shaft component 618). That is, tabs 620, 630 are urged under bias into engagement within apertures 640, 650, respectively, to engage first and second shaft components 617, 618, respectively, of shaft 612 to one another. Similarly as described above, in order to decouple shaft components 617, 618 from one another, a tool (not shown) or other implement may be used to urge tabs 620, 630 inwardly such that tabs 620, 630 are no longer disposed within apertures 640, 650, respectively. With tabs 620, 630 removed from apertures 640, 650, second shaft component 618 may be removed from lumen 614 of first shaft component 617 to decouple shaft component 617, 618 from one another.

Figure 7A:
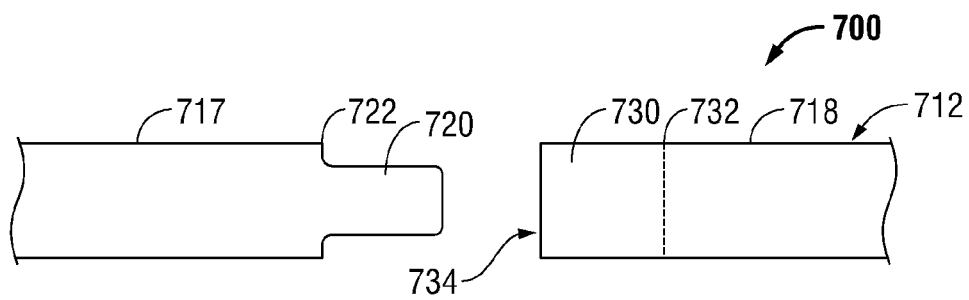
FIG. 7A is a side view of still another embodiment of a shaft coupling mechanism provided in accordance with the present disclosure wherein the shaft is in a decoupled condition.
Figure 7B:
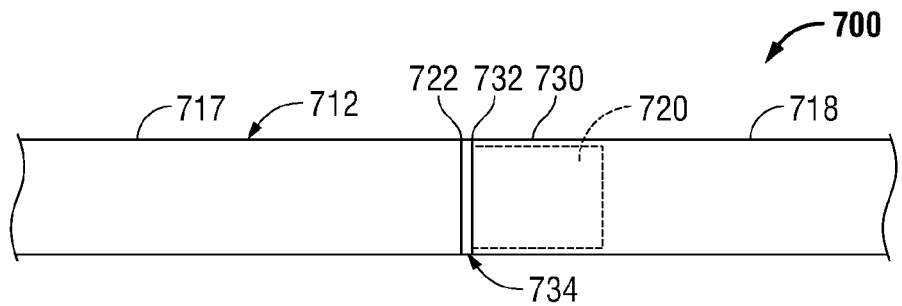
FIG. 7B is a side view of the shaft coupling mechanism of FIG. 7A wherein the shaft is in an assembled condition.

Turning now to FIGS. 7A-7B, another embodiment of a tube coupling mechanism is shown generally identified by reference numeral 700. Tube coupling mechanism 700 is configured to engage first and second shaft component 717, 718, respectively, of shaft 712 to one another. One of the shaft components, e.g., first shaft component 717, includes an insertion portion 720 extending from end 722 thereof, while the other shaft component, e.g., second shaft component 718, includes a receiving portion 730 disposed at end 732 thereof. Insertion portion 720 is configured for insertion into lumen 734 of receiving portion 730 for securing first and second shaft components 717, 718, respectively, to one another.

As shown in FIG. 7A, insertion portion 720 of first shaft component 717 defines a diameter that is smaller relative to the diameter of receiving portion 730 of shaft component 718, such that insertion portion 720 may be inserted into lumen 734 of receiving portion 730 until ends 722, 732 of first and second shaft components 717, 718, respectively, are abutting one another, as shown in FIG. 7B. Thereafter, insertion portion 720 and/or receiving portion 730 are transitioned from this first condition, wherein the diameter of insertion portion 720 is smaller than the diameter of receiving portion 730, to a second, or engaged condition, wherein insertion portion 720 is retained in engagement within receiving portion 730 via friction-fitting. As can be appreciated, in the engaged condition, the diameters of insertion portion 720 and receiving portion 730 may be substantially similar to one another to retain first and second shaft components 717, 718, respectively, in engagement with one another.

In order to engage insertion portion 720 and receiving portion 730 to one another, one or both of the portions 720, 730 are heated, or otherwise treated to achieve the first condition; insertion portion 720 in inserted into receiving portion 730; and, finally, insertion portion 720 and/or receiving portion 730 are transitioned to the engaged condition to engage first and second shaft components 717, 718, respectively, to one another. For example, receiving portion 730 of second shaft component 718 may be heated to an expanded state (i.e., the first condition) such that insertion portion 720 of first shaft component 717 may be inserted into lumen 734 of receiving portion 730. Thereafter, receiving portion 730 is cooled, or allowed to cool, such that receiving portion 730 is contracted about insertion portion 720 back to its initial condition to engage insertion portion 720 therein.

Alternatively, insertion portion 720 and receiving portion 730 may be formed from materials having different coefficients of expansion such that both insertion portion 720 and receiving portion 730 may be heated to permit insertion portion 720 to be inserted into receiving portion 730. Thereafter, both insertion portion 720 and receiving portion 730 are allowed to cool, or are cooled, back to their initial states to engage insertion portion 720 within receiving portion 730. Insertion portion 720 and/or receiving portion 730 may also be formed form shape memory materials, or may include thermal or electric bimetal materials disposed thereon to facilitate transitioning of insertion portion 720 and receiving portion 730 between the first and second conditions for securing first and second shaft components 717, 718, respectively, to one another.

In order to decouple first and second shaft components 717, 718, respectively, from one another, one or both of insertion portion 720 and receiving portion 730 are transitioned, e.g., heated, to once again achieve the first condition, thus allowing first and second shaft components 717, 718 to be translated apart from one another such that insertion portion 720 is removed from lumen 734 of receiving portion 730.

Figure 8:
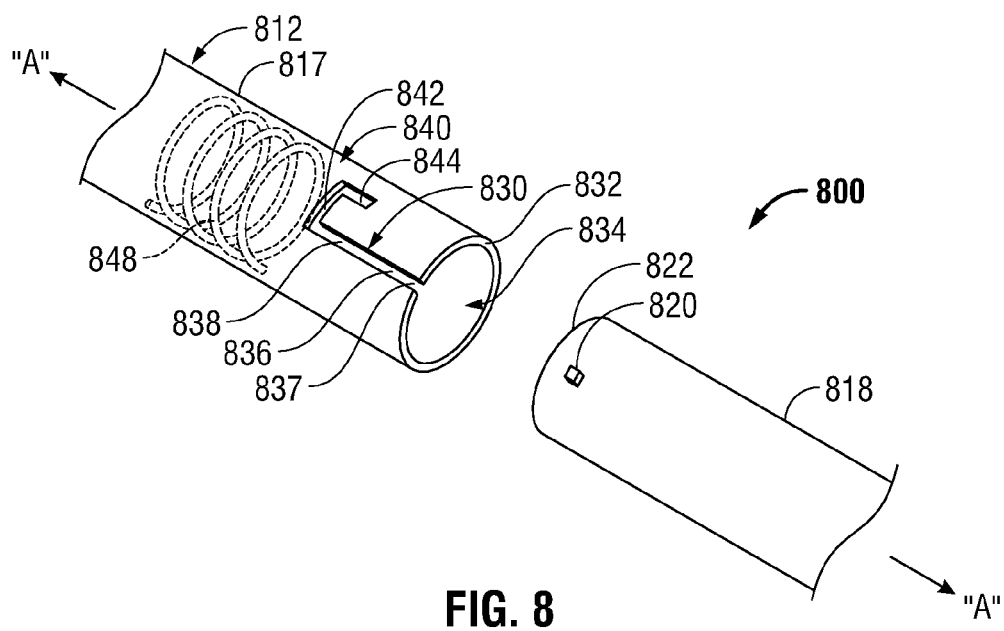
FIG. 8 is a side, perspective view of yet another embodiment of a shaft coupling mechanism provided in accordance with the present disclosure wherein the shaft is in a decoupled condition.

FIG. 8 shows another embodiment of a shaft coupling mechanism 800 that is configured to releasably engage first and second shaft components 817, 818, respectively, of shaft 812 to one another. Shaft coupling mechanism 800 generally includes a tab 820 disposed on and extending from an outer periphery of one of the shaft components, e.g., second shaft component 818, and a slot 830 defined within the outer periphery of the other shaft component, e.g., first shaft component 817. Slot 830 includes a longitudinal segment 836 having an open distal end 837 at distal end 832 of first shaft component 817 and a locking segment 840 in communication with longitudinal segment 836 at proximal end 838 thereof. Locking segment 840 includes a transverse portion 842 extending in substantially-transverse relation relative to longitudinal segment 836, and a distally-extending tab-retaining portion 844 in communication therewith. First shaft component 817 further includes a biasing member, e.g., a spring 848 disposed within lumen 834 thereof, the importance of which will be described below.

With continued reference to FIG. 8, second shaft component 818 defines a diameter smaller than that of first shaft component 817 to permit passage of second shaft component 818 into lumen 834 of first shaft component 817. Further, tab 820 of second shaft component 818 is configured to be received within, and to translate through slot 830 of first shaft component 817 to engage first and second shaft components 817, 818, respectively, to one another.

In order to engage first and second shaft components 817, 818, respectively, to one another, second shaft component 818 is inserted into lumen 834 of first shaft component 817 such that tab 820 is inserted into longitudinal segment 836 of slot 830 via open distal end 837 thereof. As second shaft component 818 is translated further into lumen 834 of first shaft component 817, tab 820 is translated proximally along longitudinal segment 836 of slot 830 towards proximal end 838 thereof. However, prior to tab 820 reaching proximal end 838 of longitudinal segment 836 of slot 830, proximal end 822 of second shaft component 818 contacts biasing member 848. As such, in order to translate second shaft component 818 further through lumen 834 of first shaft component 817, second shaft component 818 must be urged sufficiently to overcome the bias of biasing member 848.

Eventually, second shaft component 818 is translated proximally, against the bias of biasing member 848, such that tab 820 is disposed at proximal end 838 of longitudinal segment 836 of slot 830. Once this position is achieved, second shaft component 818 is rotated about longitudinal axis "A-A" relative to first shaft component 817 such that tab 820 is translated along transverse portion 842 of locking segment 840 into position adjacent tab-retaining portion 844 of locking segment 840 of slot 830. Thereafter, second shaft component 818 may be released, allowing biasing member 848 to bias second shaft component 818 distally such that tab 820 is translated distally into tab-retaining portion 844 of locking segment 840 of slot 830 to engage first and second shaft components 817, 818, respectively, to one another.

In order to disengage first and second shaft components 817, 818, respectively, from one another, second shaft component 818 is translated proximally relative to first shaft component 817 such that tab 820 is translated proximally from tab-retaining portion 844 of locking segment 840 into transverse portion 842 of locking segment 840 of slot 830. Thereafter, second shaft component 818 is rotated relative to first shaft component 817 about longitudinal axis "A-A" such that tab 820 is once again aligned with longitudinal segment 836 of slot 830 so that second shaft component 818 can be translated distally and removed from first shaft component 817, thereby decoupling first and second shaft components 817, 818, respectively, from one another.

Figure 9:
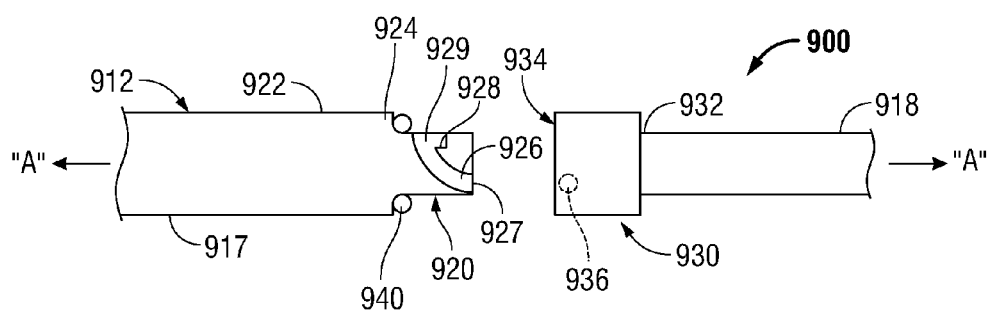
FIG. 9 is a side view of still yet another embodiment of a shaft coupling mechanism provided in accordance with the present disclosure wherein the shaft is in a decoupled condition.

Referring now to FIG. 9, shaft coupling mechanism 900 is configured to engage first and second shaft components 917, 918, respectively, of shaft 912 to one another. Shaft coupling mechanism 900 includes a first hub 920 disposed on one of the shaft components, e.g., first shaft component 917, and a second hub 930 disposed on the other shaft component, e.g., second shaft component 918. More specifically, first hub 920 extends from distal end 922 of first shaft component 917 and defines a reduced diameter relative to first shaft component 917 such that a distally-facing shoulder 924 is defined therebetween. Further, first hub 920 includes a helical track 926 defined within an outer periphery thereof, the helical track 926 including an open distal end 927 and a retaining notch 928 formed at proximal end 929 thereof. An O-ring 940, or other suitable resilient biasing member, is disposed about first hub 920 adjacent shoulder 924.

Second hub 930 extends from proximal end 932 of second shaft component 918 and defines a lumen 934 extending therethrough that is configured to receive first hub 920 of first shaft component 917 therein. Second hub 930 further includes a tab 936 disposed on an inner surface thereof and extending inwardly into lumen 934. Tab 936 is configured to be received within, and to translate through track 926 of first hub 920.

In use, to couple first and second shaft components 917, 918, respectively, to one another, first and second shaft components 917, 918 are translated toward one another until first hub 920 extends partially into second hub 930 such that tab 936 enters open distal end 927 of track 926. With tab 936 positioned within track 926, second shaft component 918 is rotated relative to first shaft component 917 about longitudinal axis "A-A" such that tab 936 is translated proximally through track 926, thereby further engaging first hub 920 within second hub 930. Upon further rotation of second shaft component 918 relative to first shaft component 917 and, thus, upon further translation of first hub 920 into second hub 930, tab 936 is translated through track 926 into position adjacent retaining notch 928 of track 926. However, in this position, second hub 930 is positioned adjacent O-ring 940. Thus, in order to translate tab 936 into notch 928, second shaft component 918 is rotated with sufficient urging to compress O-ring 940, thus permitting further proximal translation of tab 936 through helical track 926. Ultimately, once tab 936 has reached notch 928, second shaft component 918 may be released, allowing O-ring 940 to resiliently return to its at rest condition such that second shaft component 918 is biased distally and, thus, tab 936 is biased into engagement within notch 928 to engage first and second shaft components 917, 918, respectively, to one another.

In order to decouple first and second shaft components 917, 918, respectively, from one another, second shaft component 918 is translated proximally relative to first shaft component 917 such that second shaft component 918 is urged against first O-ring 940 to compress O-ring 940, allowing second shaft component 918 to translate further proximally. In this position, tab 936 of second shaft component 918 is once again aligned with helical track 926 such that second shaft component 918 may be rotated about longitudinal axis "A-A" to translate tab 936 distally through helical track 926, ultimately disengaging first and second shaft components 917, 918, respectively, from one another.

Figure 10:
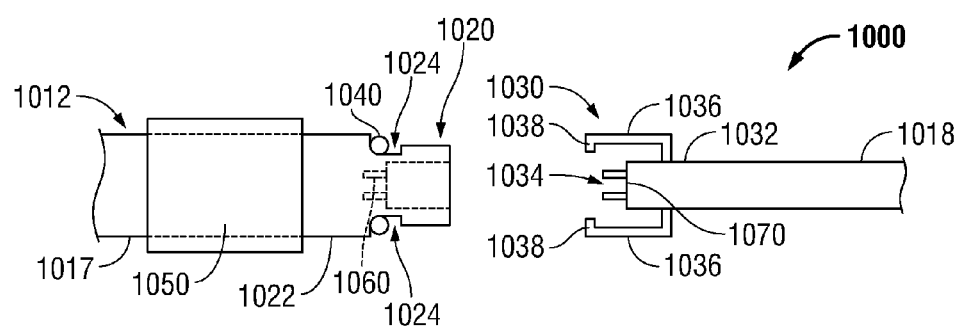
FIG. 10 is a side view of another embodiment of a shaft coupling mechanism provided in accordance with the present disclosure wherein the shaft is in a decoupled condition.

FIG. 10 shows another embodiment of a shaft coupling mechanism 1000 configured for releasably engaging first and second shaft components 1017, 1018, respectively, of shaft 1012 to one another. Shaft coupling mechanism 1000 includes a first hub 1020 disposed on one of the shaft components, e.g., first shaft component 1017, and a second hub 1030 disposed on the other shaft component, e.g., second shaft component 1018. Shaft coupling mechanism 1000 further includes a sleeve 1050 slidably disposed about shaft 1012, the importance of which will be describe below.

First hub 1020 of shaft coupling mechanism 1000 extends from distal end 1022 of first shaft component 1017 and defines a pair of opposed notches 1024 within the outer periphery thereof. Alternatively, rather than notches 1024, an annular groove (not shown) may be defined therein. An O-ring 1040, or other suitable biasing member is disposed about first shaft component 1017 and is disposed within each of notches 1024.

Second hub 1030 extends from proximal end 1032 of second shaft component 1018 and defines a lumen 1034 extending therethrough that is configured to receive first hub 1020 of first shaft component 1017 therein. Second hub 1030 further includes a pair of opposed cantilever springs 1036 extending proximally therefrom. Each of the cantilever springs 1036 defines a tab 1038 at a free end thereof. Tabs 1038 extend inwardly toward one another and are configured for engagement within notches 1024 of first hub 1020. Alternatively, rather than a pair of opposed cantilever spring 1036, second hub 1030 may include an annular biasing member (not shown) configured for engagement within an annular groove (not shown) defined within first hub 1020.

First and second hubs 1020, 1030 may each further include complementary electrical connection members 1060, 1070, respectively. More specifically, one of the first and second hubs, e.g., first hub 1020, may include a female connection member 1060, while the other hub, e.g., second hub 1030, includes a male connection member 1070 configured for insertion into female connection member 1060 to electrically couple first and second shaft components 1017, 1018, respectively, to one another, thus permitting energy to be supplied from the energy source (not explicitly shown) to end effector assembly 100 (FIG. 1).

In order to engage first and second components 1017, 1018, respectively, of shaft 1012 to one another, first and second component 1017, 1018 of shaft 1012 are brought into approximation with one another. As first and second components 1017, 1018 of shaft 1012 are brought into approximation with one another, tabs 1038 of cantilever springs 1036 are flexed outwardly, i.e., apart from one another, to permit passage first hub 1020 into lumen 1034 of second hub 1030.

As first hub 1020 is inserted further into lumen 1034 of second hub 1030, tabs 1038 are translated proximally along the outer periphery of first hub 1020. Eventually, tabs 1030 are translated into position adjacent notches 1024 defined within first hub 1020. Once disposed adjacent notches 1024, the resilient biasing force of cantilever springs 1036 urges tabs 1038 inwardly back toward their initial position such that tabs 1038 are engaged within notches 1024, thereby engaging first and second shaft components 1017, 1718 to one another. O-ring 1040, which is also disposed within notches 1024, biases tabs 1038 into frictional engagement within notches 1024, ensuring sufficiently engagement therebetween. Translation of first hub 1020 further into lumen 1034 of second hub 1030 also translates male connection member 1070 into engagement with female connection member 1060 to electrically couple first and second shaft components 1017, 1018, respectively, to one another.

With first and second shaft components 1017, 1018, respectively, engaged to one another, sleeve 1050 may be slid distally about shaft 1012 to substantially surround first and second hubs 1020, 1030, respectively. As can be appreciated, with sleeve 1050 disposed about first and second hubs 1020, 1030, sleeve 1050 helps maintain the engagement between first and second shaft components 1017, 1018, respectively.

In order to disengage first and second shaft components 1017, 1018, sleeve 1050 is first slid proximally (or distally) such that sleeve 1050 is no longer disposed about first and second hubs 1020, 1030, respectively. Thereafter, tabs 1038 are disengaged from notches 1024 and first and second shaft components 1017, 1018 are translated apart from one another, thus disengaging first and second shaft components 1017, 1018 from one another.

Figure 11:
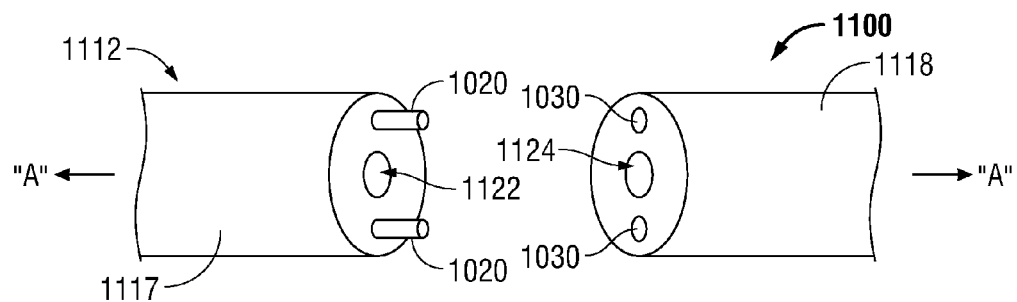
FIG. 11 is a side view of another embodiment of a shaft coupling mechanism provided in accordance with the present disclosure wherein the shaft is in a decoupled condition.

FIG. 11 shows another embodiment of a tube coupling mechanism 1100 configured to releasably engage first and second components 1117, 1118 of shaft 1112 to one another. Shaft components 1117, 1118 each include a lumen 1122, 1124 extending therethrough. More specifically, lumens 1122, 1124 are configured to cooperate with one another to permit reciprocation of drive sleeve 60 (FIGS. 2A-2C) and/or knife bar 182 (FIGS. 2A-2C) therethrough to facilitate moving jaw members 110, 120 (FIGS. 2A-2C) between the spaced-apart position and the approximated position and for translating knife 184 (FIGS. 2A-2C) between the retracted position and the extend position, respectively.

With continued reference to FIG. 11, one of the shaft components, e.g., first shaft component 1117, includes a pair of pins 1020 extending distally therefrom, while the other shaft components, e.g., second shaft component 118 includes a pair of apertures 1130 defined therethrough. Pins 1020 and apertures 1030 are radially-spaced from lumens 1122, 1124, respectively, so as not to interfere with the internal components of shaft 1112. Pins 1020 are configured to be inserted into apertures 1030 to secure first and second shaft components to one another. More specifically, pins 1020 define a substantially similar, or slightly smaller, diameter than that of apertures 1030 to facilitate friction-fitting engagement between first and second shaft components 1117, 1118, respectively. Further, pins 1020 may include a resilient material disposed on the outer periphery thereof (or may be formed from a resilient material or structure), and/or apertures 1030 may also include a resilient material disposed on the internal surface thereof. In such an embodiment, pins 1020 and/or apertures 1030 are configured to be compressed upon insertion of pins 1030 and/or apertures 1030 to resiliently bias first and second shaft components 1117, 1118 to one another.

Figure 12:
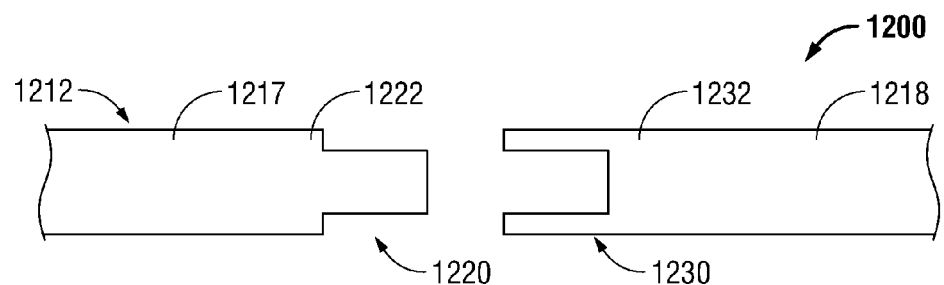
FIG. 12 is a side view of another embodiment of a shaft coupling mechanism provided in accordance with the present disclosure wherein the shaft is in a decoupled condition.

Turning now to FIG. 12, yet another embodiment of a tube coupling mechanism configured for engaging first and second shaft components 1217, 1218, respectively, of shaft 1212 to one another is shown generally identified by reference numeral 1200. One of the shaft components, e.g., first shaft component 1217, includes a male connection member 1220 extending distally from distal end 1222 therefrom, while the other shaft component, e.g., second shaft component 1218, includes a recess, or female connection member 1230 defined therein at proximal end 1232 thereof. Male connection member 1220 and/or female connection member 1230 are shaped complementary to one another to facilitate engagement therebetween for engaging first and second shaft components 1217, 1218, respectively, to one another. Further, male connection member 1220 may include an adhesive disposed on an outer peripheral surface thereof (or may be formed from an adhesive material) and/or female connection member 1230 may include an adhesive disposed on an inner surface thereof (or may be formed from an adhesive material) to facilitate engagement therebetween. More specifically, the adhesive may include UV-activated adhesives, heat-activated adhesives, pressure-activated adhesives, gamma ray-activated adhesives, solvent adhesives, or other suitable adhesives. Alternatively, temporary welding may be used to secure first and second shaft components 1217, 1218, respectively, to one another. A cleaning solution (not shown), removal instrument (not shown) or any other suitable mechanism may be used for disengaging the adhered components 1217, 1218.

Figure 13:
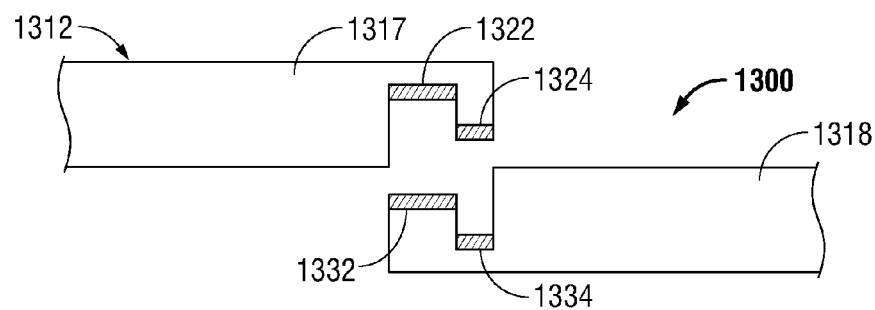
FIG. 13 is a side, cross-sectional view of still another embodiment of a shaft coupling mechanism provided in accordance with the present disclosure wherein the shaft is in a decoupled condition.

With reference now to FIG. 13, tube coupling mechanism 1300 is shown configured for releasably engaging first and second shaft components 1317, 1318, respectively, of shaft 1312 to one another. Tube coupling mechanism 1300 includes one or more magnets 1322, 1324 imbedded within, coupled to, or disposed on first shaft component 1317 and one or more magnets 1332, 1334 imbedded within, coupled to, or disposed on second shaft component 1318. Magnets 1322, 1332 are complementarily-shaped relative to one another and are oriented to define opposite polarities at the exposed surfaces thereof. Similarly, magnets 1324, 1334 are complementarily-shaped relative to one another and are oriented to define opposite polarities at the exposed surfaces thereof. Accordingly, upon approximation of shaft components 1317, 1318, magnets 1322, 1332 are attracted to one another, and magnets 1324, 1334 are attracted to one another to engage first and second shaft components 1317, 1318, respectively, to one another. Further, as shown in FIG. 13, magnets 1322, 1324 and magnets 1332, 1334 are offset relative to one another and are positioned to define a keyed-configuration, thus inhibiting rotation or disengagement of first and second shaft components 1317, 1318, respectively, from one another in response to axial and/or rotational loading thereof.

Figure 14:
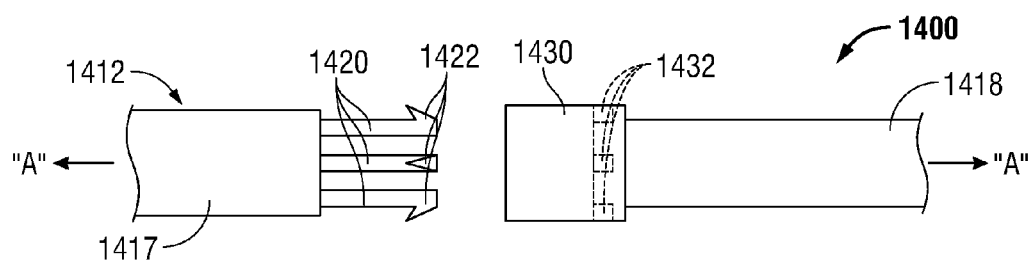
FIG. 14 is a side view of yet another embodiment of a shaft coupling mechanism provided in accordance with the present disclosure wherein the shaft is in a decoupled condition.

Referring now to FIG. 14, another embodiment of a tube coupling mechanism is shown generally identified via reference numeral 1400. Tube coupling mechanism 1400 is configured to releasably engage first and second components 1417, 1418 of shaft 1412 to one another. More specifically, tube coupling mechanism 1400 includes a plurality of cantilever arms 1420 disposed radially about longitudinal axis "A-A" and extending distally from one of the shaft components, e.g., first shaft component 1417, and a plurality of complementary-shaped recesses 1432 defined within hub 1430 of the other shaft component, e.g., second shaft component 1418. Similarly as described above with respect to previous embodiments, tabs 1422 extending from cantilever arms 1420 are configured for engagement within recesses 1432 of hub 1430 upon approximation of first and second shaft components 1417, 1418, respectively, to engage first and second shaft components 1417, 1418 to one another.

Figure 15:
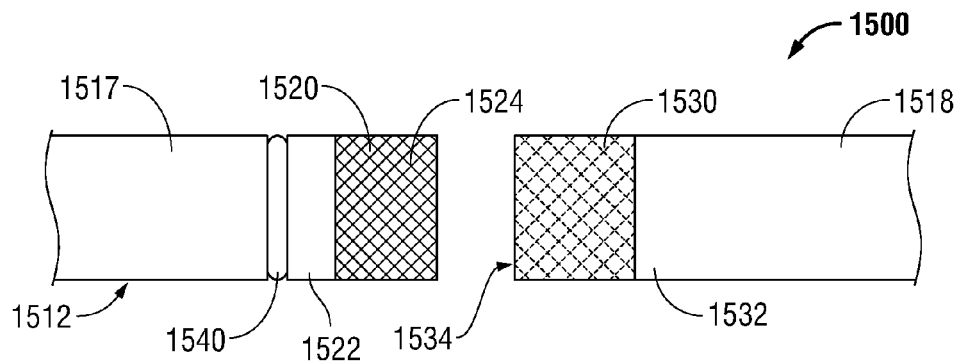
FIG. 15 is a side view of still yet another embodiment of a shaft coupling mechanism provided in accordance with the present disclosure wherein the shaft is in a decoupled condition.

Turning now to FIG. 15, tube coupling mechanism 1500 is configured to releasably engage first and second shaft components 1517, 1518, respectively, of shaft 1512 to one another. One of the shaft components, e.g., first shaft component 1517, includes an insertion portion 1520 extending from distal end 1522 thereof, while the other shaft component, e.g., second shaft component 1518, includes a receiving portion 1530 disposed at proximal end 1532 thereof that is configured to receive insertion portion 1520 therein for releasably engaging first and second shaft component 1517, 1518, respectively, to one another. Further, a release ring 1540 is disposed on first shaft component 1517 and is longitudinally slidable thereabout to permit disengagement of first and second shaft components 1517, 1518, as will be described below.

Continuing with reference to FIG. 15, insertion portion 1520 of first shaft component 1517 defines a diameter that is slightly smaller than a diameter of lumen 1534 of receiving portion 1530 of second shaft component 1518 to permit insertion of insertion portion 1520 into lumen 1534 of receiving portion 1530 and to retain insertion portion 1520 in engagement within receiving portion 1530 via friction-fitting. Further, insertion portion 1520 defines a textured outer peripheral surface 1524 configured to facilitate engagement of insertion portion 1520 within lumen 1534 of receiving portion 1530.

Receiving portion 1530 of second shaft component 1518 defines a generally cylindrical configuration and is formed from a helically-wound braid, e.g., a biaxial braid, of material. Due to this braided configuration, receiving portion 1530 is elongated and constricted, i.e., the length of receiving portion 1530 is increased and the diameter of lumen 1534 is reduced, upon axial extension of receiving portion 1530. Receiving portion 1530 is normally disposed in an at-rest position, wherein receiving portion 1530 defines a relatively smaller length and wherein lumen 1534 defines a relatively larger diameter as compared to the extended position.

In use, in order to engage first and second shaft components 1517, 1518, respectively, to one another, insertion portion 1520 is inserted into lumen 1534 of receiving portion 1530. In this position, textured outer peripheral surface 1524 of insertion portion 1520 facilitates the frictional engagement of insertion portion 1520 of first shaft component 1517 within receiving portion 1530 of second shaft component 1518. Further, removal of insertion portion 1520 from receiving portion 1530 is inhibited by the braided-configuration of receiving portion 1530. More specifically, attempted withdrawal of insertion portion 1520 causes axial extension of receiving portion 1530 which, in turn, constricts, or reduces the diameter of lumen 1534 of receiving portion 1530. Accordingly, receiving portion 1530 is constricted about insertion portion 1520, thereby increasing the frictional engagement therebetween and inhibiting withdrawal of insertion portion 1520 from receiving portion 1530.

In order to disengage first and second shaft components 1517, 1518, respectively, release ring 1540 is slid distally over first shaft component 1517 into position abutting the proximal end of receiving portion 1530 of second shaft components 1518. Thereafter, while maintaining release ring 1540 in position abutting receiving portion 1530, first shaft component 1517 is translated proximally relative to second shaft component 1518 to withdraw insertion portion 1520 from receiving portion 1530, thereby disengaging first and second shaft component 1517, 1518, respectively, from one another. Release ring 1540 inhibits extension of receiving portion 1530 during withdrawal of first shaft component 1517 such that the diameter of lumen 1534 of receiving portion 1530 is maintained. In other words, release ring 1540 inhibits extension and constriction of receiving portion 1530, thus permitting disengagement of of first and second shaft components 1517, 1518, respectively, from one another.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a shaft defining a longitudinal axis therethrough and having an end effector assembly disposed at a distal end thereof, the shaft including first and second shaft components that are releasably engagable with one another, the first shaft component including an insertion portion having an outer cylindrical surface circumscribing the first shaft component, the second shaft component including a receiving portion having an inner cylindrical surface circumscribing a lumen of the second shaft component, the lumen configured to receive the insertion portion of the first shaft component therein, the outer cylindrical surface of the first shaft component configured to frictionally engage the inner cylindrical surface of the second shaft component, the receiving portion configured to constrict about the insertion portion upon translation of the insertion portion apart from the receiving portion to inhibit withdrawal of the insertion portion, thereby maintaining the engagement between the first and second shaft components.

2. The surgical instrument according to claim 1, wherein the receiving portion defines a braided configuration configured to elongate and reduce a diameter of a lumen extending therethrough upon extension of the receiving portion.

3. The surgical instrument according to claim 1, wherein the insertion portion defines a textured outer peripheral surface configured to facilitate frictional engagement between the insertion portion and the receiving portion.

4. The surgical instrument according to claim 1, further comprising a release ring disposed about the first shaft component, the release ring slidable about the first shaft component into position adjacent the receiving portion of the second shaft component to inhibit constriction of the receiving portion about the insertion portion, thereby permitting withdrawal of the insertion portion from the receiving portion to disengage the first and second shaft components from one another.

5. The surgical instrument according to claim 1, wherein the first and second shaft components are configured to permit translation of a drive sleeve therethrough for transitioning the end effector assembly between a first state and a second state.

6. The surgical instrument according to claim 5, further comprising:
    a knife assembly disposed within the drive sleeve, the knife assembly including a knife bar having a knife disposed at a distal end of the knife bar, the knife bar longitudinally translatable through the shaft and relative to the end effector assembly to translate the knife between a retracted position and an extended position for cutting tissue.

* * * * *